United States Patent
Li et al.

(10) Patent No.: US 8,380,311 B2
(45) Date of Patent: Feb. 19, 2013

(54) HOUSING FOR IMPLANTABLE MEDICAL DEVICE

(75) Inventors: Bernard Q. Li, Plymouth, MN (US); John J. Grevious, Minneapolis, MN (US); Timothy J. Davis, Coon Rapids, MN (US); Leroy Perz, Buffalo, MN (US); Chris J. Paidosh, St. Anthony, MN (US)

(73) Assignee: Medtronic, Inc., Minneapolis, MN (US)

( * ) Notice: Subject to any disclaimer, the term of this patent is extended or adjusted under 35 U.S.C. 154(b) by 1047 days.

(21) Appl. No.: 11/590,250

(22) Filed: Oct. 31, 2006

(65) Prior Publication Data

US 2008/0103556 A1    May 1, 2008

(51) Int. Cl.
*A61N 1/375* (2006.01)

(52) U.S. Cl. .......................................................... 607/36

(58) Field of Classification Search ........... 607/2, 36–37
See application file for complete search history.

(56) References Cited

U.S. PATENT DOCUMENTS

| | | | |
|---|---|---|---|
| 4,041,955 A | 8/1977 | Kelly et al. | |
| 5,423,881 A * | 6/1995 | Breyen et al. | 607/122 |
| 5,470,345 A | 11/1995 | Hassler et al. | |
| 5,782,891 A | 7/1998 | Hassler et al. | |
| 5,895,414 A * | 4/1999 | Sanchez-Zambrano | 607/36 |
| 6,067,474 A | 5/2000 | Schulman et al. | |
| 6,411,854 B1 | 6/2002 | Tziviskos et al. | |
| 6,414,835 B1 * | 7/2002 | Wolf et al. | 361/302 |
| 6,516,227 B1 | 2/2003 | Meadows et al. | |
| 6,596,439 B1 | 7/2003 | Tsukamoto et al. | |
| 2002/0042630 A1 * | 4/2002 | Bardy et al. | 607/5 |
| 2002/0103510 A1 | 8/2002 | Bardy et al. | |
| 2003/0078675 A1 | 4/2003 | Daum | |
| 2003/0120320 A1 * | 6/2003 | Solom | 607/36 |
| 2004/0093039 A1 * | 5/2004 | Schumert | 607/40 |
| 2005/0075700 A1 * | 4/2005 | Schommer et al. | 607/61 |
| 2005/0107835 A1 | 5/2005 | Bardy et al. | |
| 2005/0113888 A1 | 5/2005 | Jimenez et al. | |
| 2005/0149139 A1 | 7/2005 | Plicchi et al. | |

FOREIGN PATENT DOCUMENTS

| | | |
|---|---|---|
| DE | 37 40 732 A1 | 8/1988 |
| EP | 0 099 874 | 2/1984 |
| EP | 0 534 782 A1 | 3/1993 |
| EP | 1 424 098 | 6/2004 |
| WO | WO 90/06108 | 6/1990 |
| WO | WO 95/34342 | 12/1995 |
| WO | WO 01/97908 A2 | 12/2001 |

OTHER PUBLICATIONS

Komotori, J. et al., "Corrosion response of surface engineered titanium alloys damaged by prior abrasion," *WEAR*, 2001, cover and pp. 1239-1249, vol. 251, Elsevier Science B.V.

International Search Report and Written Opinion for Application No. PCT/US2007/002042, date of mailing Sep. 28, 2007, 10 pages.

International Search Report and Written Opinion for Application No. PCT/US2007/001763, date of mailing Sep. 28, 2007, 10 pages.

(Continued)

*Primary Examiner* — Scott Getzow
*Assistant Examiner* — Amanda Patton
(74) *Attorney, Agent, or Firm* — Foley & Lardner LLP

(57) ABSTRACT

A housing for an implantable medical device includes a first portion formed from a first material and a second portion formed from a second material. The first material and the second material comprise titanium and the first material has a higher resistivity than the second material.

45 Claims, 13 Drawing Sheets

OTHER PUBLICATIONS

Amendment and Reply for U.S. Appl. No. 11/590,678, mail date Aug. 10, 2009, 7 pages.
Office Action for U.S. Appl. No. 11/590,678, mail date Nov. 25, 2009, 7 pages.
Amendment and Reply for U.S. Appl. No. 11/590,678, mail date Feb. 23, 2010, 10 pages.
Office Action for U.S. Appl. No. 11/590,678, mail date Jun. 8, 2010, 9 pages.
Request for Continued Examination and Reply for U.S. Appl. No. 11/590,678, mail date Sep. 8, 2010, 16 pages.
Office Action for U.S. Appl. No. 11/590,678, mail date Dec. 15, 2010, 10 pages.
Amendment and Reply for U.S. Appl. No. 11/590,678, mail date Apr. 15, 2011, 12 pages.
Office Action for U.S. Appl. No. 11/590,678, mail date Jun. 21, 2011, 9 pages.
Reply for U.S. Appl. No. 11/590,678, mail date Aug. 22, 2011, 13 pages.
Advisory Action for U.S. Appl. No. 11/590,678, mail date Sep. 14, 2011, 3 pages.
Request for Continued Examination and Amendment and Reply for U.S. Appl. No. 11/590,678, mail date Oct. 20, 2011, 25 pages.

* cited by examiner

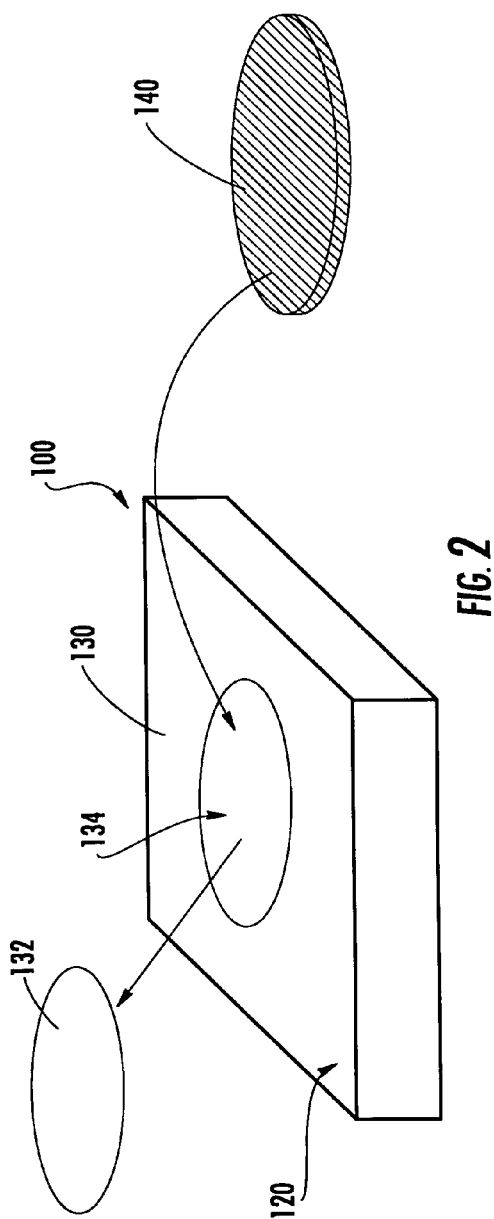
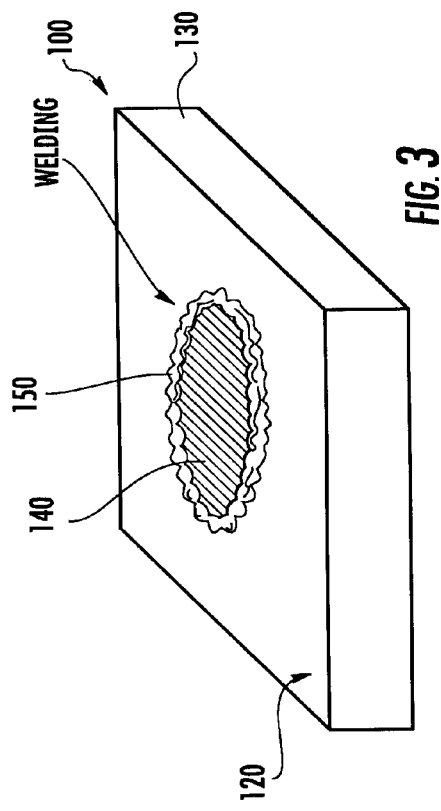

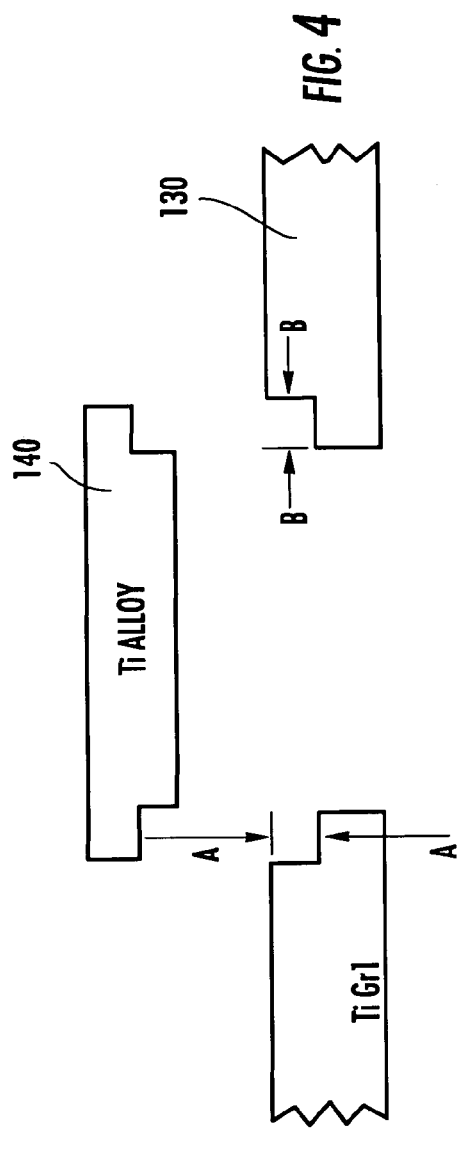
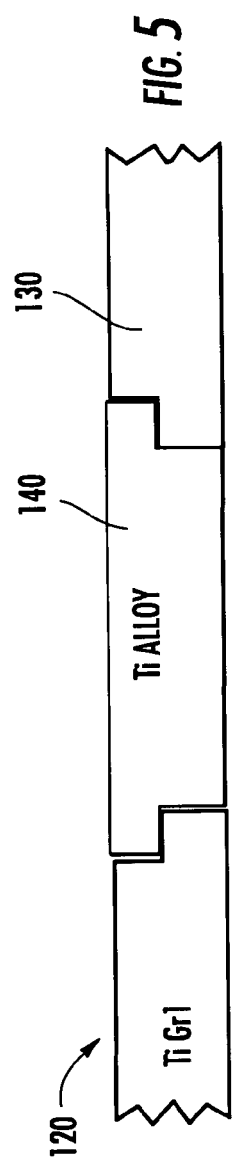
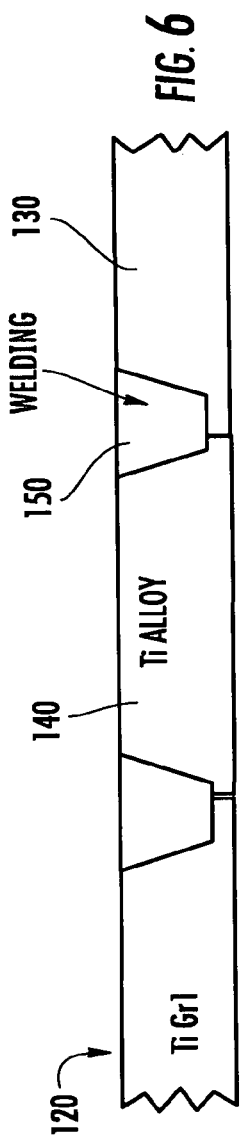
FIG. 4
FIG. 5
FIG. 6

HOUSING FOR IMPLANTABLE MEDICAL DEVICE

BACKGROUND

The present invention relates generally to the field of implantable medical devices (IMDs) such as implantable neurological stimulation (INS) devices, drug pumps, and cardiac pacemakers. More particularly, the present invention relates to implantable medical devices that include titanium alloy housings or casings.

Implantable medical devices typically include external structures (e.g., housings or casings) that are made from biologically compatible materials to minimize undesirable interactions with the human body. One example of such a biologically compatible material that has been used for IMD housings is commercial pure titanium Grade 1 (hereinafter referred to as "CP Ti Grade 1"). This material has several characteristics that make it desirable for IMD housings, including its mechanical properties, which make it possible to form relatively small structures with complex geometries.

The use of CP Ti Grade 1 may not be optimal in all IMD applications, however. For example, certain IMDs may include batteries within their housings that are designed to be inductively charged while the IMDs are implanted. In such configurations, the IMD includes an electrically conductive coil or winding that is electrically coupled to the battery of the IMD. To charge the battery, a "primary" coil or winding from a charging system is placed near the location where the IMD is implanted and a current is sent through the primary coil; through induction, a current is then generated in the secondary coil that is transmitted to the battery.

Where the coil of the IMD is provided within the housing of the IMD, the CP Ti Grade 1 material may not be ideally suited to allow inductive charging. It may be desirable instead to use a material that exhibits greater power coupling efficiency and improved telemetry distance than would be possible if the structure of the device was made using only CP Ti Grade 1. Additionally, because the IMD is typically subjected to various stresses during implantation and use, it may also be desirable to form the housing from a material that has greater strength than CP Ti Grade 1.

It would be desirable to provide an implantable medical device that utilizes a material for its housing that allows for improved power coupling and telemetry distance, and which may have sufficient mechanical strength to provide enhanced protection for the device. It would also be desirable to provide an implantable medical device that utilizes a material that may be formed in a relatively simple and cost-efficient manner at relatively low temperatures. It would be desirable to provide an implantable medical device that includes any one or more of these or other advantageous features as will be apparent to those reviewing the present disclosure.

SUMMARY

An exemplary embodiment of the invention relates to a housing for an implantable medical device that includes a first portion formed from a first material and a second portion formed from a second material. At least one of the first material and the second material comprise a titanium alloy and the first material has a higher resistivity than the second material.

Another exemplary embodiment of the invention relates to an implantable neurological stimulation device that includes a housing that includes a first portion and a second portion. A coil provided within the housing. The first portion includes a first titanium material and the second portion includes a second titanium material. The first portion is provided proximate the coil and having a higher resistivity than the second portion.

Another exemplary embodiment of the invention relates to a method of producing an implantable medical device that includes coupling a first member to a second member to form a housing. The first member comprises a first titanium material and the second member comprises a second titanium. The first material has a higher resistivity than the second titanium material. The method also includes providing a coil within the housing such that the first member is provided proximate the coil.

BRIEF DESCRIPTION OF THE DRAWINGS

FIG. 2 is a schematic perspective view of a housing or casing for an implantable medical device according to an exemplary embodiment illustrating the removal of a portion of the housing to form an aperture therein.

FIG. 3 is a schematic perspective view of the housing shown in FIG. 2 illustrating the welding of a member to the housing in the location of the aperture.

FIG. 4 is a schematic cross-sectional view of a portion of the housing shown in FIG. 3 illustrating the assembly of the housing according to an exemplary embodiment.

FIG. 5 is a schematic cross-sectional view of the portion of the housing shown in FIG. 3 illustrating the member provided in place in the aperture.

FIG. 6 is a schematic cross-sectional view of the portion of the housing shown in FIG. 3 illustrating the welding of the member to the housing.

DETAILED DESCRIPTION

Figure 1:
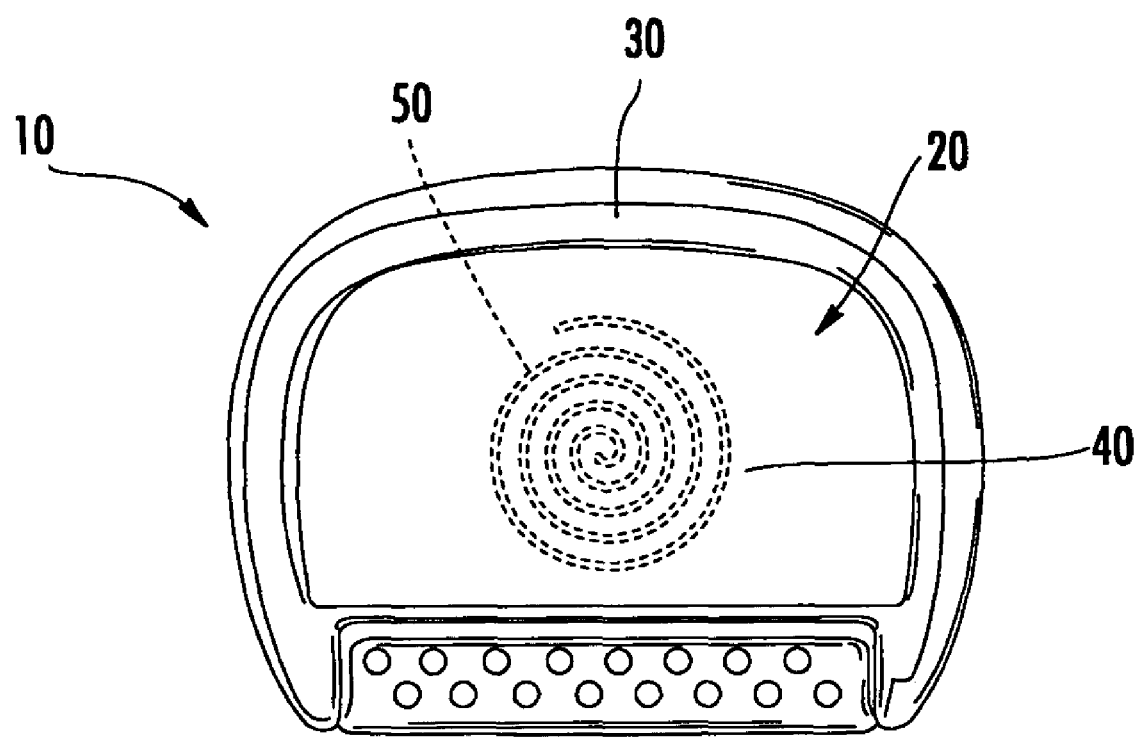
FIG. 1 is a plan view of a housing or casing for an implantable medical device according to an exemplary embodiment.

Referring to FIG. 1, a housing or casing 20 for an implantable medical device (IMD) 10 in the form of an implantable neurological stimulation (INS) device is shown according to an exemplary embodiment. The housing 20 is intended to protect the IME 10 from damage during implantation and use, and is formed of a biocompatible material to prevent undesirable interactions between the IMD 10 and the human body or other organism into which it is implanted. As will be described in greater detail below, the subject matter described herein may also find utility in other types of IMDs according to other exemplary embodiments, including drug pumps, cardiac pacemakers, and the like.

According to an exemplary embodiment, the IMD 10 includes a coil or winding 50 that is used to charge the EMD 10 by induction when another coil coupled to a charging device is provided proximate the IMD 10. In this manner, the IMD 10 may be recharged without the need to remove it from the body in which it is implanted (i.e., the charging may occur transdermally). According to an exemplary embodiment, the coil is provided inside the housing 20. According to other exemplary embodiments, the coil may be provided outside the housing.

According to an exemplary embodiment, the housing 20 is formed from at least two different materials. For example, as shown in FIG. 1, a first portion 30 of the housing 20 is formed from a first material and a second portion 40 of the housing 20 is formed from a second material. According to an exemplary embodiment, the second portion 40 is a generally flat or planar member that is coupled to the first portion 30 by welding, adhesive, or other means. The first portion 30 forms the remainder of the housing. While the embodiment illustrated in FIG. 1 illustrates the use of two materials to form the housing 20, according to other exemplary embodiments, a different number of materials may be used (e.g., the housing may have three or more different sections, each formed from a different material). It should also be understood that while FIG. 1 illustrates a particular configuration for an MD housing, other types of housings having different sizes, shapes, and configurations may also be used according to other exemplary embodiments.

FIG. 2 is a schematic view of a housing 120 according to an exemplary embodiment illustrating the removal of a portion 132 of the housing 120, which leaves an opening or aperture 134 provided in the remaining portion 130 of the housing 120. As illustrated in FIG. 2, portion 132 is generally circular in shape, although the portion 132 may have any desired size or shape according to other exemplary embodiments.

Any suitable method may be used to remove the portion 132 from the housing 120. According to an exemplary embodiment, an electrical discharge machining (EDM) process may be used. According to other exemplary embodiments, other techniques may be used (e.g., cutting using a water jet, a laser, etc.). According to yet still other exemplary embodiments, the aperture 134 may be formed in the housing 120 when the housing is produced (e.g., the housing is molded with the aperture already in place), thus eliminating the need to remove the portion 132 therefrom.

As shown in FIG. 3, a member or element shown as a second portion 140 is coupled to the portion 130 of the housing 120 at the location of the aperture 134 such that the housing is effectively sealed. According to an exemplary embodiment, the portion 140 is coupled to the portion 130 of the housing 120 by welding (weldments are labeled with reference numeral 150 in FIG. 3). According to various exemplary embodiments, various welding methods of coupling portion 140 to the portion 130 of the housing 120 may be used (e.g., resist welding, stir friction welding, laser welding, etc.). Portion 140 is formed from a material that differs from that of the portion 120 according to an exemplary embodiment.

Portion 140 may be formed by cutting it from a larger sheet of material. In certain situations, portion 140 may have a tendency after it is cut to bend upward due to the residual stresses within the material. In such a case, a hot sizing process such as that described in U.S. patent application Ser. No. 11/413,471 filed Apr. 28, 2006 (incorporated by reference herein in its entirety) may be used to provide portion 140 as a substantially flat component.

FIGS. 4-6 illustrate the steps used in a method of forming the housing 120 according to an exemplary embodiment. In FIG. 4, the portion 140 is aligned with the aperture 134 such that the portion 140 may be coupled to the portion 130 as illustrated in FIG. 5. According to an exemplary embodiment, the portion 130 of the housing includes a cutout configured (e.g., has a "stepped" configuration) for engaging a complementary portion of the portion 140 as the portion 140 is put in place. These cutouts may be formed, for example, by machining the components to remove material to form the geometries shown in FIG. 4. The height of the cutout (as illustrated by arrows "A") is between approximately 0.001 and 0.0012 inches and the width of the cutout (as illustrated by arrows "B") is between approximately 0.001 and 0.0012 inches according to an exemplary embodiment, although it should be understood that other dimensions may be used with various other exemplary embodiments.

As illustrated in FIG. 6, once the portion 140 is in place, weldments 150 are formed to couple the portion 140 to the portion 130 of the housing 120. In this manner, the housing 120 is formed as having two separate portions (e.g., portions 130 and 140), each formed from different materials.

For certain portions of the housing, it is it is advantageous to select materials that have relatively high tensile yield strengths (to provide improved strength of the housing) while still exhibiting relatively good formability at relatively low temperatures (to allow the manufacture of relatively small components having relatively complex geometries at temperatures between approximately 200° and 400° C., and more preferably at a temperature of approximately 500° C.). One advantageous feature of using an alloy that exhibits relatively good formability at relatively low temperatures is that the occurrence of undesirable oxidation during the forming operation may be reduced or eliminated.

Figure 7:
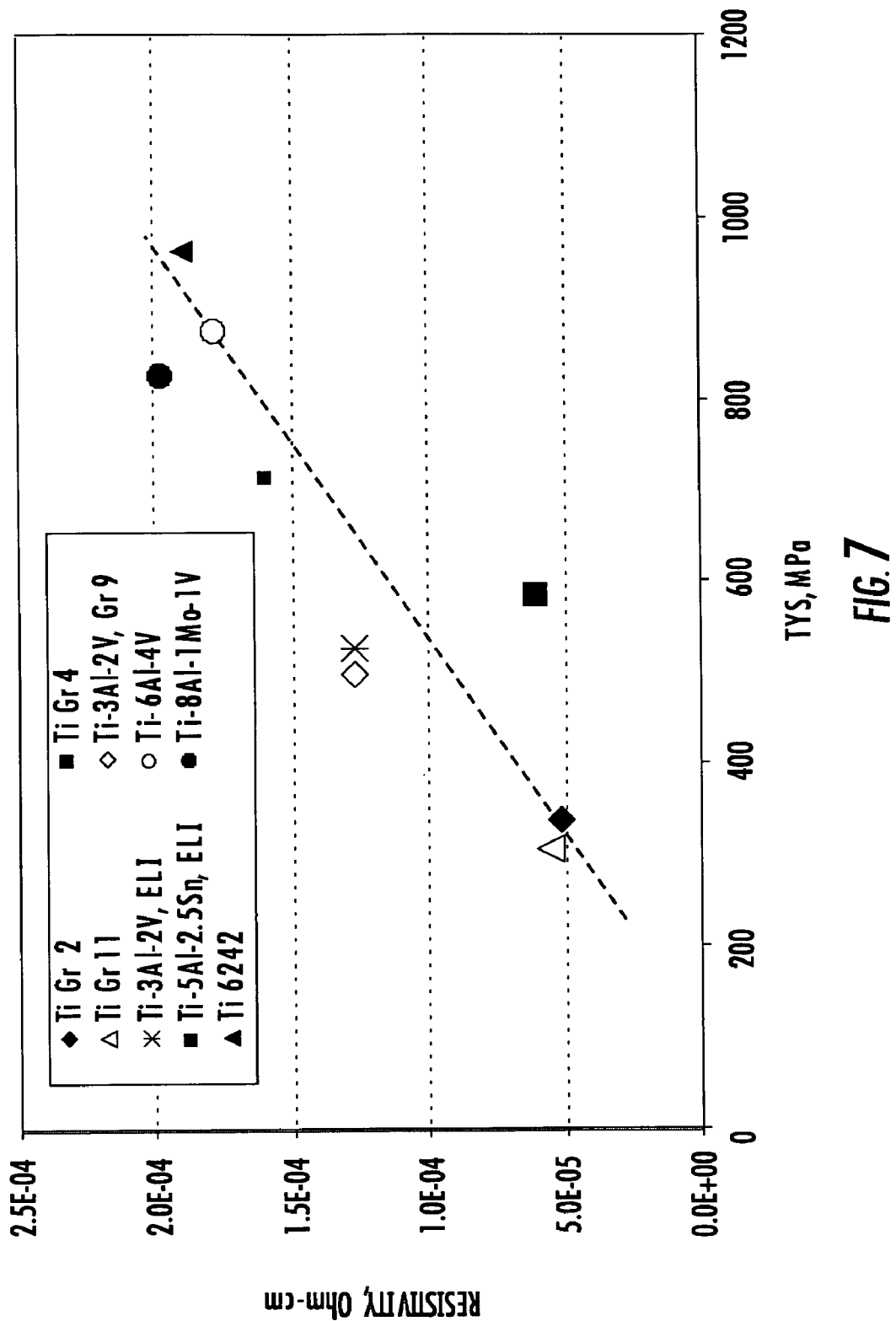
FIG. 7 is a graph illustrating the relationship between resistivity and tensile yield strength for a number of titanium alloys.
Figure 8:
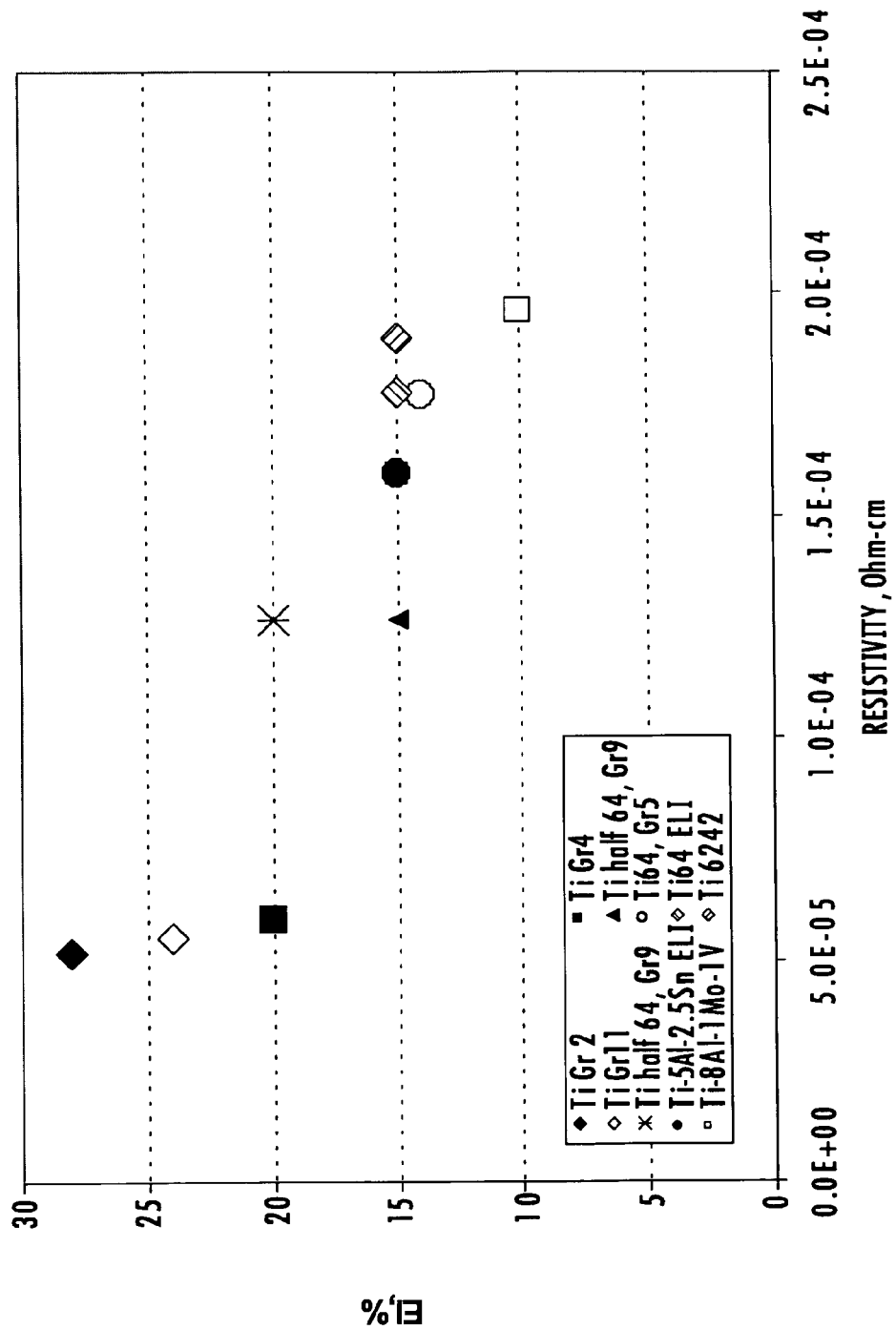
FIG. 8 is a graph illustrating the relationship between resistivity and percent elongation for a number of titanium alloys.

FIG. 7 is a graph illustrating the relationship between resistivity and tensile yield strength for a number of titanium alloys, and FIG. 8 is a graph illustrating the relationship between formability (shown as percent elongation of the alloys) and resistivity of such alloys. From this data, it is evident that resistivity of titanium alloys tends to increase with increasing tensile yield strength. Conversely, the resistivity tends to decrease with increasing formability.

It is generally understood that the tensile yield strength of titanium alloys generally increases with increasing alloy content. Based on this fact and the relationships illustrated in FIGS. 7 and 8, one would expect that titanium alloys having relatively high alloy content will have relatively high tensile yield strengths and resistivities, but will be less formable than alloys having lower alloy contents.

Figure 9:
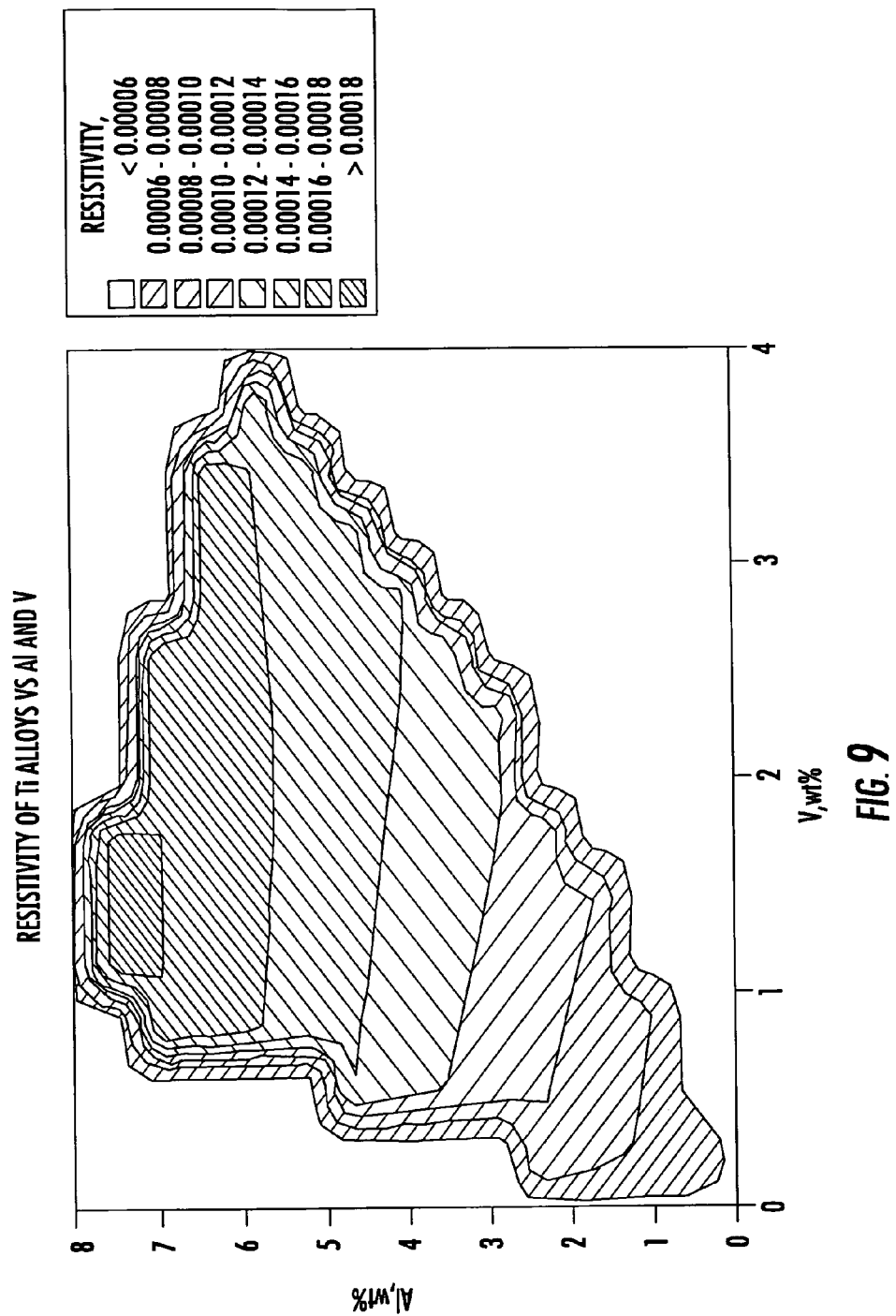
FIG. 9 is a contour plot illustrating the effect of varying amounts of aluminum and vanadium on the resistivity of titanium alloys.
Figure 10:
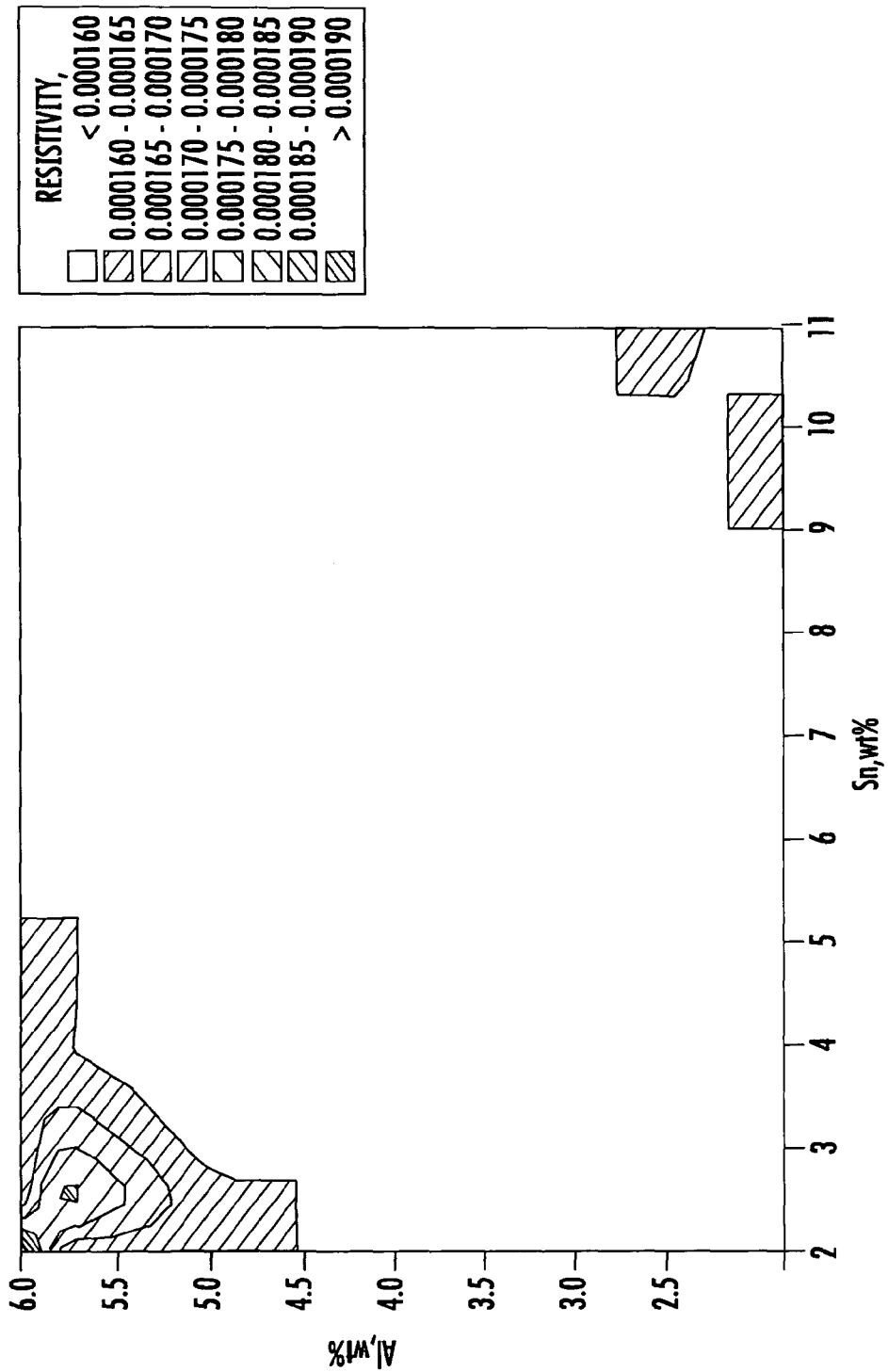
FIG. 10 is a contour plot illustrating the effect of varying amounts of aluminum and tin on the resistivity of titanium alloys.

While the amount of alloying elements is understood to have an effect on the yield strength (and thus the resistivity) of the titanium alloys, different alloying elements have been shown to affect the resistivity of titanium alloys differently. For example, FIG. 9 is a contour plot illustrating the change in resistivity for titanium-aluminum-vanadium alloys when the percentages of aluminum and vanadium are varied. In contrast, FIG. 10 is a contour plot illustrating the change in resistivity for titanium-aluminum-tin alloys when the percentages of aluminum and tin are varied. As can be seen from these contour plots, the effect on resistivity is different when the aluminum/vanadium percentages are varied as compared to the difference resulting from varying the aluminum/tin percentages.

Where the material will be used to form a portion of the IMD housing that has a relatively thin wall and/or may have a relatively complex geometry, it is also beneficial for the alloy selected to have relatively good formability performance to allow the alloy to be formed into relatively thin sheets that may be formed into structures having relatively complex geometries (e.g., structures having relatively small features and sharp corners). For example, according to an exemplary embodiment, at least a portion of the housing (e.g., a "corner" of the housing) has a radius of curvature of between approximately 0.1 and 2.5 millimeters.

It should be noted that there are various tests available to characterize the relative formability of different alloys, including tensile tests (both longitudinal and transverse) intended to measure the percent elongation of the alloy, bending tests, and the like. It will be understood by those reviewing this disclosure that whether an alloy is sufficiently formable for a particular application will depend on a variety of factors, including the size and shape of the device to be formed, the temperature at which such forming will be performed, and other factors. For example, in the case of implantable medical devices such as the IMD 10 illustrated in FIG. 1, a subjective determination may be made as to the formability of various alloys. For such applications, preferred alloys for such an application will have a percent elongation at a temperature of approximately 25° C. of greater than approximately 13 percent and may be rolled into sheets having thicknesses of between approximately 0.007 and 0.016 inches (e.g., between approximately 0.007 and 0.012 inches).

As described above, according to an exemplary embodiment, the housing 20 is formed from at least two different materials (e.g., portion 40 is formed from a different material that portion 30 as shown in FIG. 1). One advantageous feature of forming the housing from multiple different materials is that the housing may be tailored to allow enhanced power coupling and recharging efficiency, improved telemetry distance, reduced heating effects during magnetic resonance imaging (MRI), and improved tolerance for compression stress as compared to devices that have housings or casing formed only from a single material such as CP Ti Grade 1.

According to an exemplary embodiment, a portion of the housing (e.g., portion 40 as shown in FIG. 1) is formed from a material that has a higher resistivity than another portion (e.g., portion 30) of the housing. For example, the higher-resistivity material may have a resistivity of between approximately 100 μmΩ-cm and 210 μmΩ-cm and a tensile yield strength of between approximately 65 ksi and 150 ksi. It is intended that the portion of the housing having the higher resistivity will be aligned with a recharge or telemetry coil provided within the housing to allow for improved power coupling efficiency and telemetry distance for the IMD.

According to a particular exemplary embodiment, a portion of the housing is formed from CP Ti Grade 1, while another portion of the housing is formed from another titanium material having a higher resistivity than CP Ti Grade 1. According to an exemplary embodiment, both portions of the housing are formed from titanium materials (e.g., alloys) other than CP Ti Grade 1, in which case one of the titanium materials may have a higher resistivity than the other.

Any of a number of titanium materials may be used to form portions of the housing. According to an exemplary embodiment, a portion of the housing is made from a titanium (Ti) alloy having the general formula Ti—Al—B—C where B represents one or more alloy elements such as V, Sn, Mo, Nb, Zr, and combinations thereof and C represents one or more impurity elements such as N, C, H, Fe, O, Si, Pd, Ru, and combinations thereof. Aluminum is provided in an amount between approximately 2 and 7 weight percent according to an exemplary embodiment. Elements represented by B and C in the above formula may be present in amounts shown in Table 1 according to various exemplary embodiments.

TABLE 1

| Element | Approximate Weight Percent |
|---|---|
| V | 2-6 |
| Sn | 1.5-6.5 |
| Mo | <6 |
| Nb | <2 |
| Zr | <5 |
| N | <0.05 |
| C | <0.1 |
| H | <0.0015 |
| Fe | <2 |
| O | <0.3 |
| Si | <0.5 |
| Pd | <1 |
| Ru | <0.02 |

According to a particular exemplary embodiment, a portion of the housing may be formed from a titanium alloy having the formula Ti-6Al-4V (referred to as Ti64). Such an alloy has a greater tensile yield strength than CP Ti Grade 1 and also has better power coupling efficiency and improved telemetry distance.

Other titanium alloys may also be used according to other exemplary embodiments. For example, a portion of the housing may be formed from a titanium alloy having a composition of Ti-4.5Al-3V-2Fe-2Mo-0.15O. One example of such an alloy is commercially available from JFE Steel Corporate of Chiba, Japan under the trade name SP-700. Based on known properties of this alloy, it is believed that such a material will be sufficiently biocompatible to allow its use in implantable medical devices such as INS devices, while also providing enhanced power coupling and recharging efficiency, improved telemetry distance, reduced heating effects during magnetic resonance imaging (MRI), and improved tolerance for compression stress.

Figure 11:
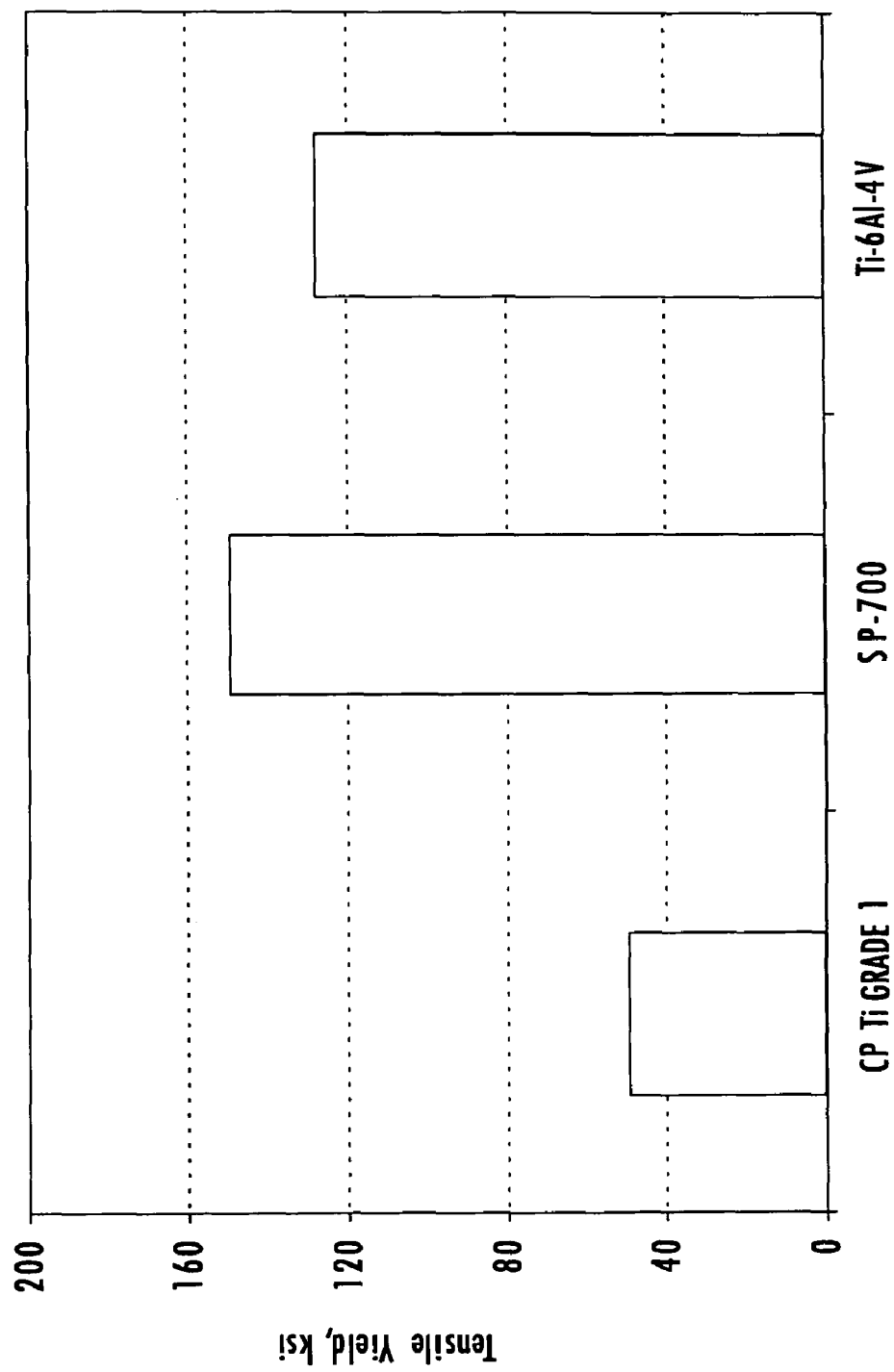
FIG. 11 is a graph illustrating a comparison of tensile yield strengths of various titanium alloys.

FIG. 11 is a graph illustrating the tensile yield strength of SP-700 alloy as compared to CP Ti Grade 1 and Ti-6Al-4V alloys. As shown, the SP-700 alloy has a tensile yield strength that is approximately three times greater than CP Ti Grade, 1 and also has a higher tensile yield strength than the Ti-6Al-4V alloy. It is intended that this property of the SP-700 alloy will contribute to enhanced strength of the resulting INS packaging and improved resistivity.

Figure 13:
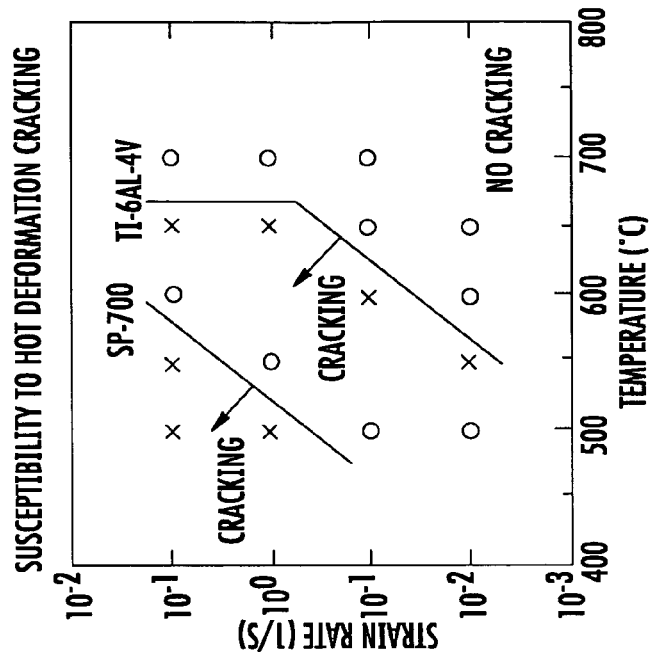
FIG. 13 is a graph illustrating the relationship between strain rate and temperature responses for two titanium alloys.
Figure 12:
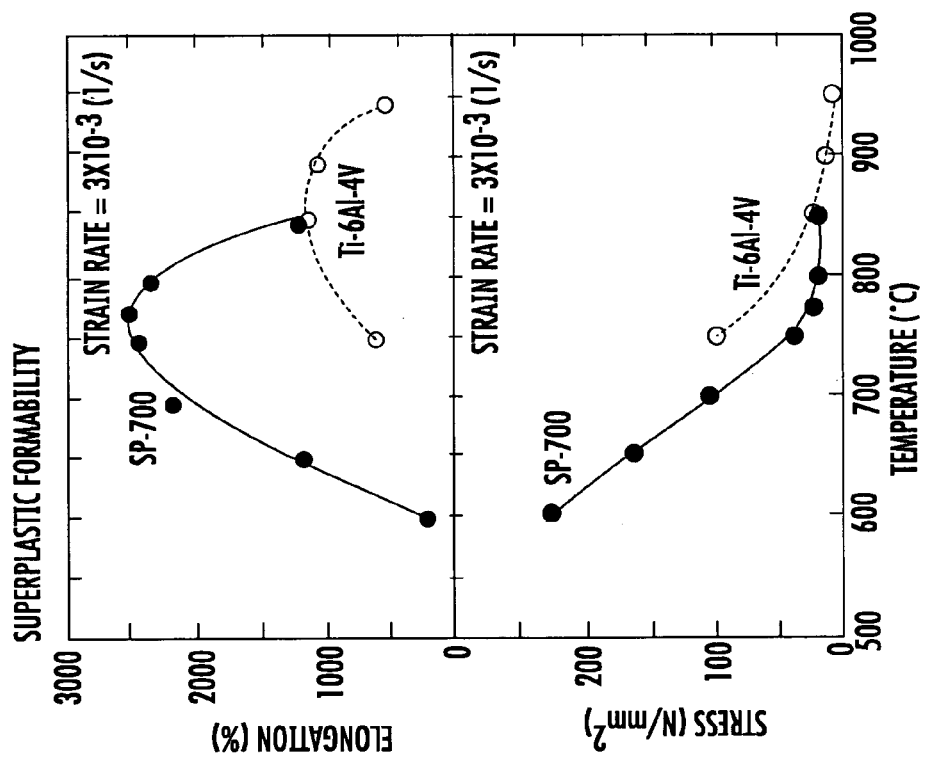
FIG. 12 is a graph illustrating the relationship of percent elongation and stress versus temperature responses for two titanium alloys.

An additional advantageous feature of the SP-700 alloy is that it has a relatively small grain size that allows it to be superplastically deformed at a relatively low temperature (e.g., approximately 775° C.). FIG. 12 is a graph illustrating the relationship between percent elongation and temperature for the SP-700 alloy and the Ti-6Al-4V alloy. As evident from the graph, the SP-700 alloy is significantly more formable at lower temperatures as compared to the Ti-6Al-4V alloy. It is intended that by using the SP-700 alloy, relatively thin (<0.4 mm) sheets of the material may be produced which may be formed into housings for INS devices that have relatively complex geometries or shapes. Additionally, as illustrated in FIG. 13, the SP-700 alloy is less susceptible to hot deformation cracking as compared to Ti-6Al-4V alloys.

According to other exemplary embodiments, other titanium alloys may be used to form portions of the housing. One such alloy is commercially available from Allvac of Albany, Oreg. under the trade name ATI425 and having a composition of Ti-4Al-2.5V-1.5Fe-0.25O. According to other exemplary embodiments, titanium alloys such as Ti-6Al-2Sn-4Zr-2Mo (Ti6242), Ti-3Al-2.5V (Grade 9), and titanium matrix composites (alpha and near alpha titanium matrix with SiC, TiC, TiO particles distributed therein) may be used. It should also be noted that a Ti-8Al—Mo—V (Ti811) alloy may be used in configurations where a portion of the housing is relatively flat (Ti811 alloy is not as formable as the other alloys described above, but has excellent resistivity values, as illustrated in Table 2 below; accordingly, Ti811 may be used to form portions of housings such as portion 40 illustrated in FIG. 1).

Figure 14:
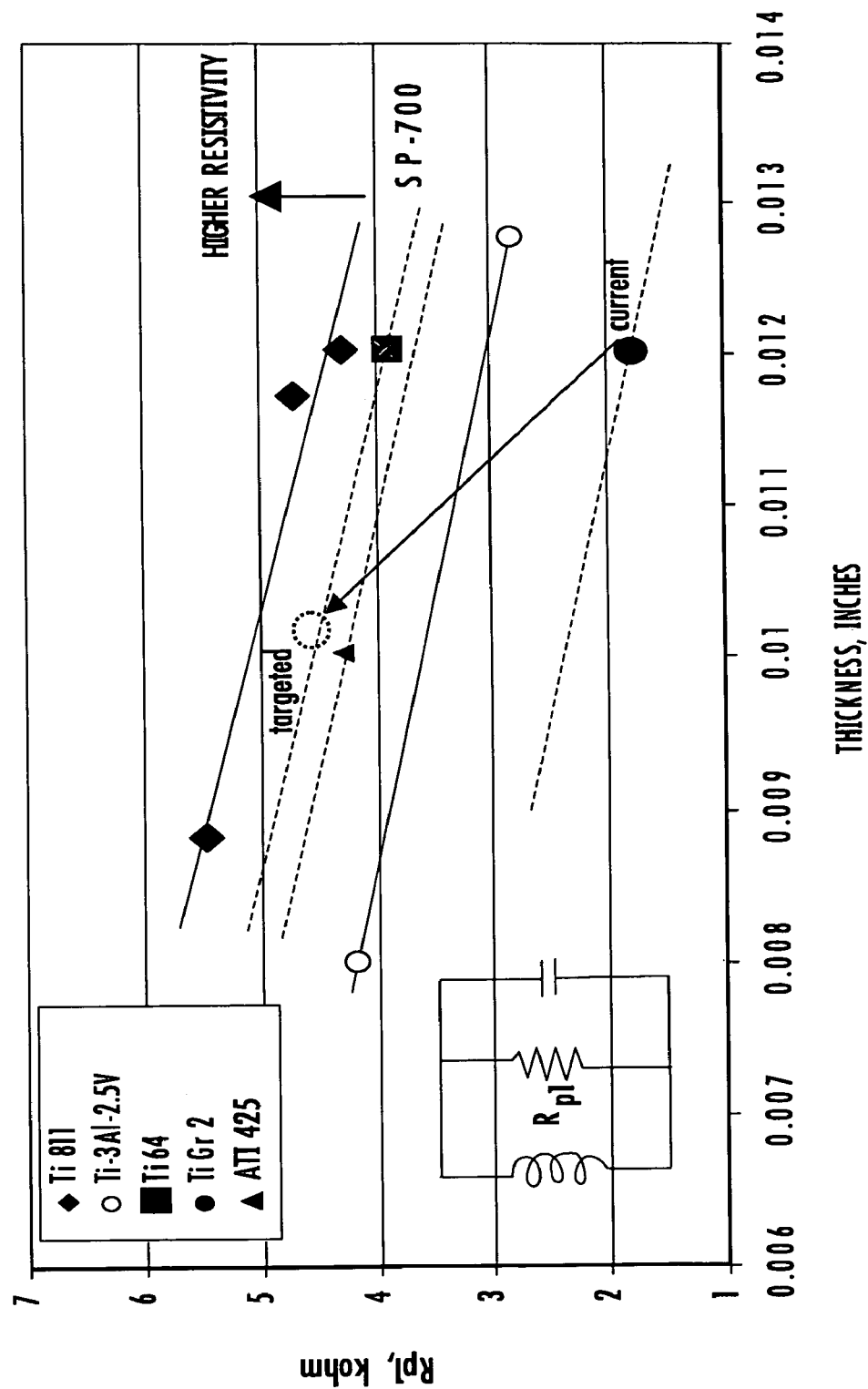
FIG. 14 is a graph illustrating the relationship between effective parallel coil resistance and sheet thickness for a number of titanium alloys.
Figure 15:
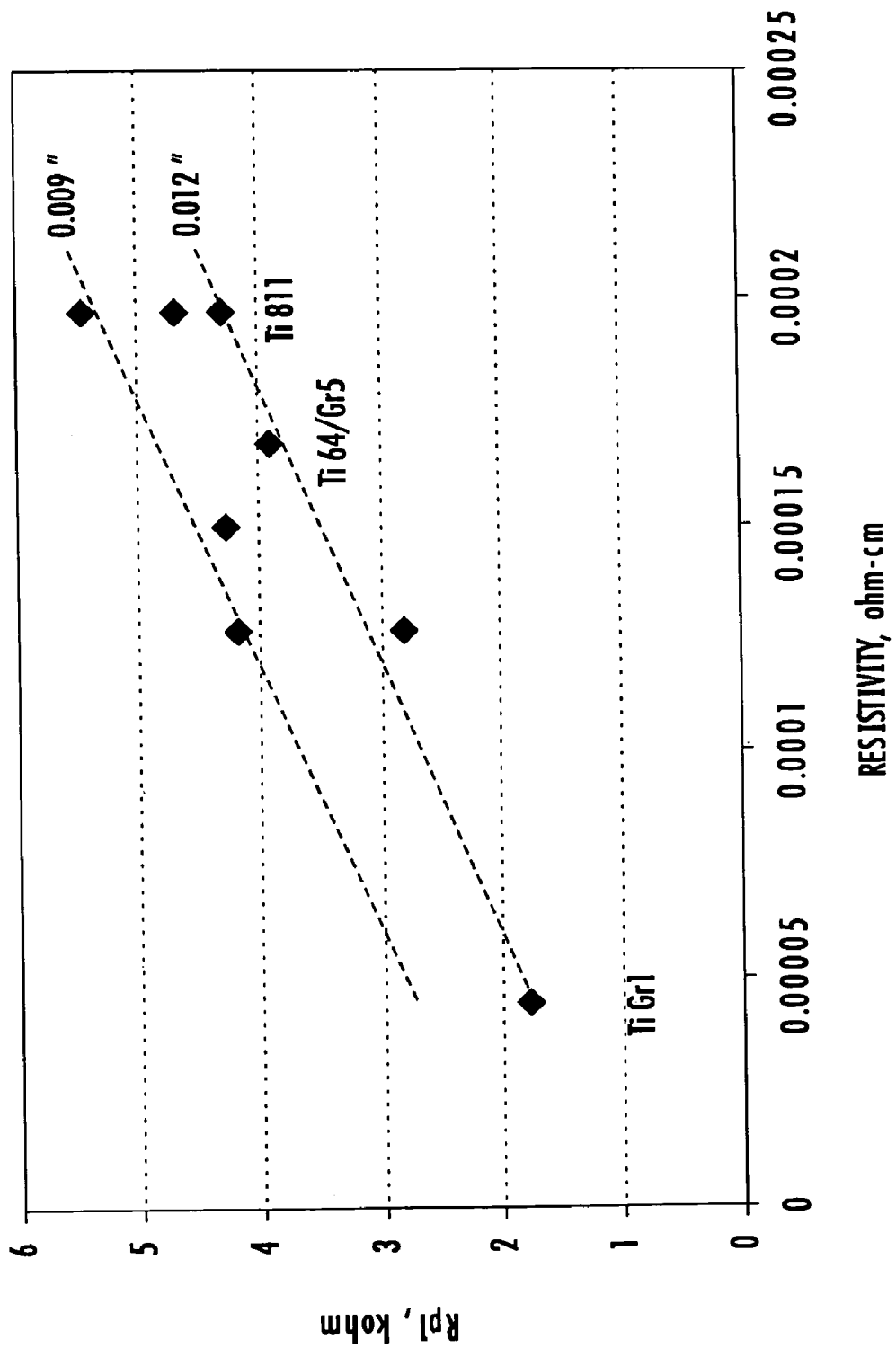
FIG. 15 is a graph illustrating the relationship between effective parallel coil resistance and resistivity for a number of titanium alloys.
Figure 16:
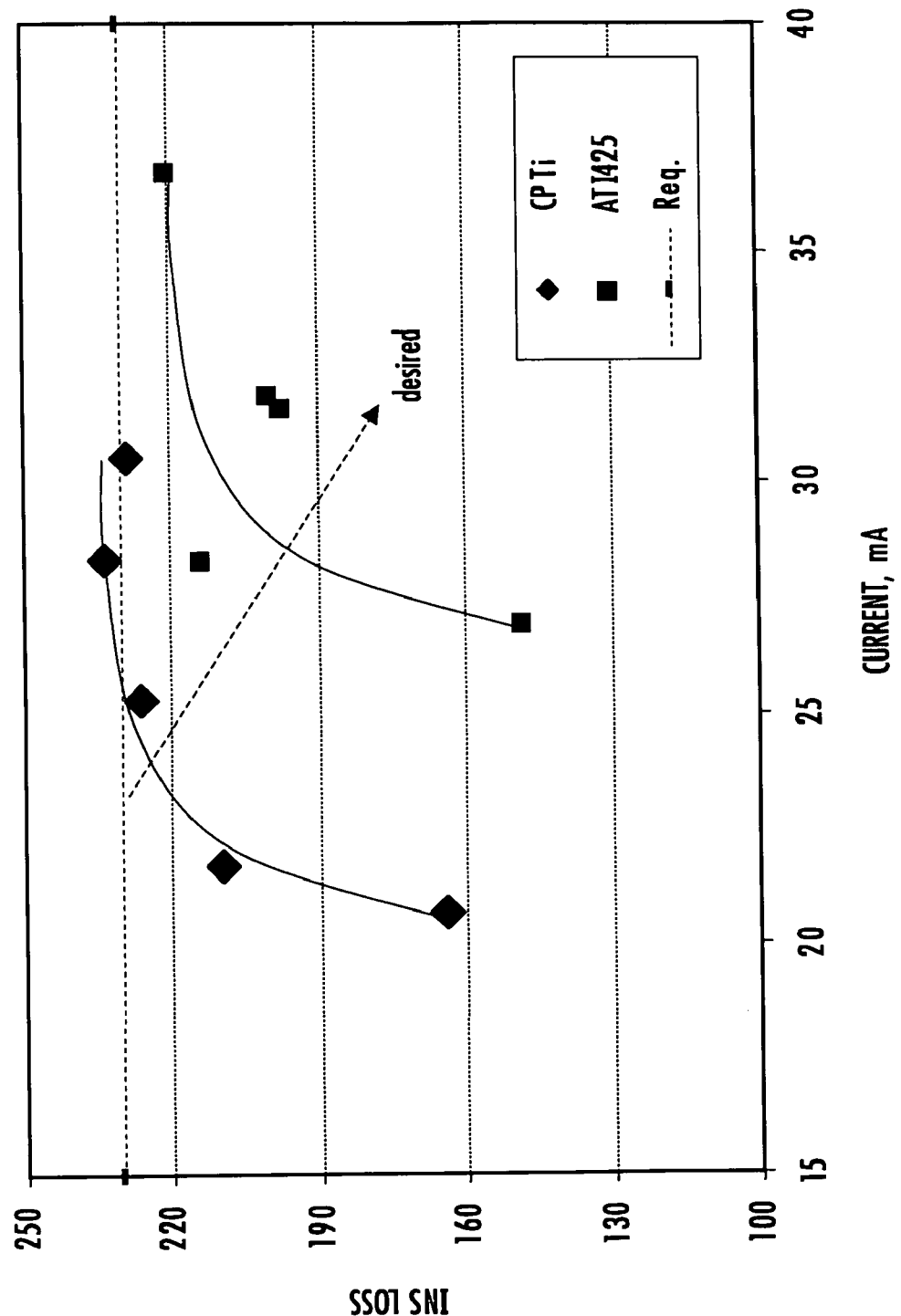
FIG. 16 is a graph illustrating the relationship between INS loss and current for two titanium alloys.

FIG. 14 illustrates the relationship between the effective parallel coil resistance (Rp1) and housing thickness for housings formed from various titanium alloys at a charging frequency of 175 kHz. As shown in FIG. 15, the effective parallel coil resistance tends to decrease with increasing housing thickness. As shown in FIG. 16, the effective parallel coil resistance also tends to increase with increasing resistivity; thus, one would expect that alloys having relatively high resistivities will also exhibit relatively good effective parallel coil resistance.

By using higher resistivity alloys and a thinner gauge sheet of material, an effective parallel coil resistance of as much as three times that of CP Ti Grade 1 alloy may be achieved. Additionally, it should be noted that housings formed from the Ti811 alloy exhibit effective parallel coil resistance that is comparable to or greater than housings formed from the Ti-6Al-4V alloy, while housings formed from the ATI425

TABLE 2

| Alloy | Tensile Yield Strength (ksi) | Percent Elongation | Resistivity (μmOhm-cm) | Bend Ratio (R/t) | Cold Rolling Reduction Limit (%) | Formability | Sheet Thickness (inches) |
|---|---|---|---|---|---|---|---|
| CP Ti Gr 1 | 32 | 25 | 45 | 1.5 | >80 | Excellent | 0.001 |
| Ti—6Al—4V | 130 | 11 | 168 | 4 | 20 | Not good | 0.016 |
| SP-700 | 134 | 21 | 164 | 2.1 | 58-69 | Good | 0.007 |
| ATI425 | 127 | 18 | | 2.1 | Similar to SP-700 | Good | 0.007 |
| Ti—3Al—2.5V (Gr 9) | 72 | 20 | 125 | 2.1 | 60-80 | Very Good | 0.01 |
| Ti811 | 140 | 10 | 198 | 4.5 | Worse than Ti-6Al-4V | Worst of group | 0.5 |
| Target | 120 | >12 | 125-200 | <3 | >50 | — | <0.012 |

Table 2 illustrates properties of the titanium alloys described above. The particular material selected may depend on the desired characteristics of the IMD, the size and shape of the IMD housing, and other factors. For example, while both the SP-700 and Ti-6Al-4V alloys have higher resistivities and tensile yield strengths as compared to CP Ti Grade 1, the SP-700 alloy has significantly better percent elongation, formability (a subjective measure), and cold rolling reduction limit as compared to the Ti-6Al-4V alloy, which allows it to be formed into sheets that are significantly thinner than those formed from the Ti-6Al-4V alloy (e.g., sheets having a thickness of 0.007 as opposed to sheets having a thickness of 0.016). Accordingly, it may be more desirable to use the SP-700 alloy for portions of housings that require complex geometries or relatively thin sections, although the Ti-6Al-4V may also be used in other configurations as may be desired.

Those reviewing this disclosure will recognize that various combinations are possible. For example, as described above, a housing may include a first portion formed from CP Ti Grade 1 and another portion made from a titanium alloy such as Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V. According to another embodiment, a housing may include a two portions that are each formed from a different titanium alloy (such as those described in the preceding sentence), where one of the materials has a higher resistivity than the other. According to other exemplary embodiments, one or more portions of the housing may be made from an alloy comprising a plurality of titanium alloys (e.g., two or more alloys selected from Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V). Again, the particular materials selected may vary depending on the intended application and other factors.

alloy exhibit effective parallel coil resistance that is less than those formed from the Ti-6Al-4V alloy. Because the resistivity of the SP-700 alloy is comparable to that of the Ti-6Al-4V alloy, it is expected that the effective parallel coil resistance of these two alloys will also be similar.

FIG. 16 illustrates the relationship between current and the INS loss for devices having housings made using two different alloys. As illustrated in FIG. 16, the devices having housings formed from the ATI425 alloy exhibit less INS loss at given amounts of current as compared to those having housings formed from the CP Ti Grade 1 alloy. As a result, it is expected that housings formed from ATI425 alloys would exhibit improved charging efficiency as compared to those formed from Ti Grade 1 alloys.

Figure 17:
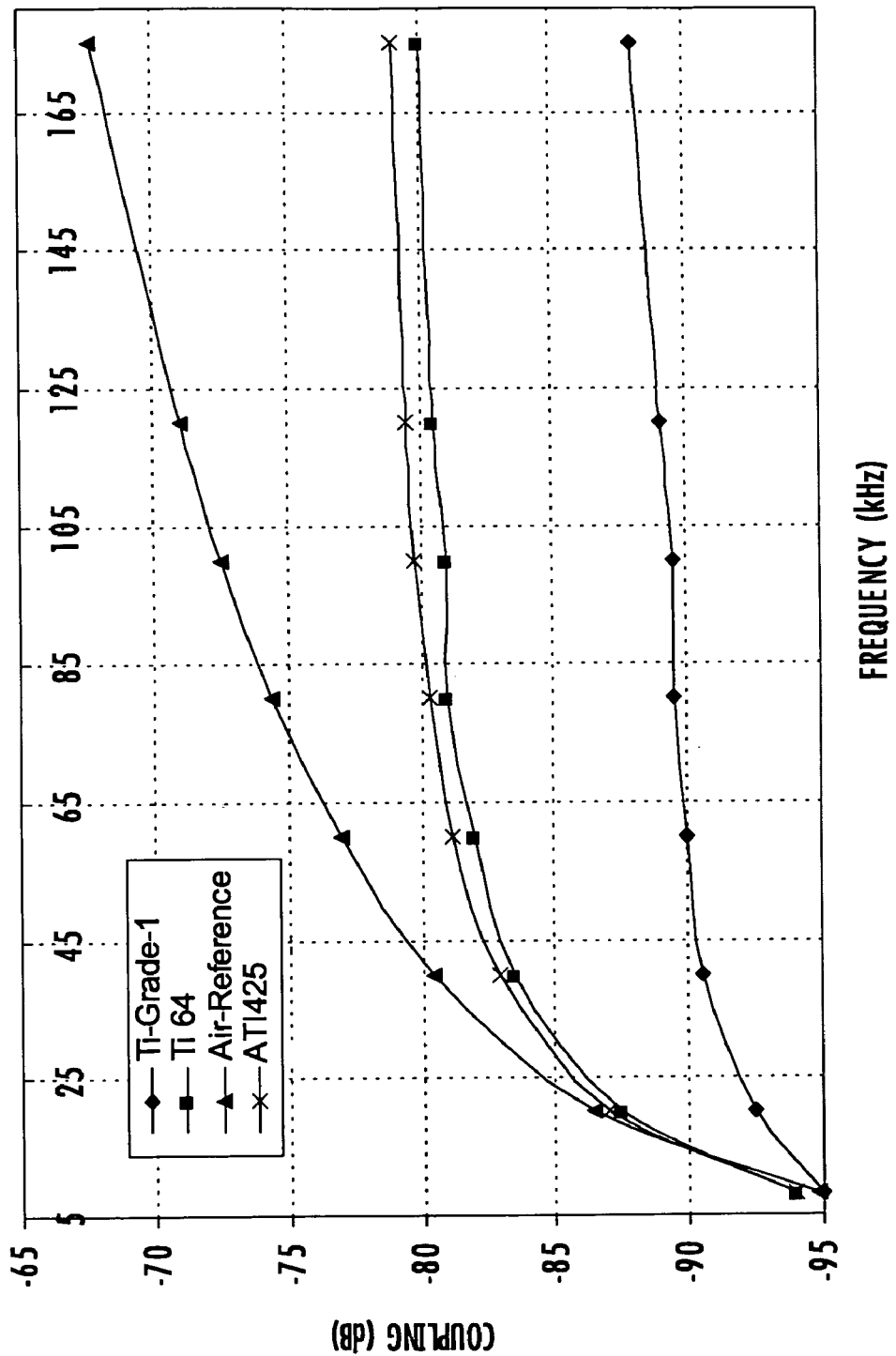
FIG. 17 is a graph illustrating the relationship between charging frequency and coil coupling response for various titanium alloys.

FIG. 17 illustrates the relationship between charging frequency and coil coupling for devices having housings formed from various titanium alloys. The coil voltage coupling from 8 kHz to 175 kHz was first measured for a ten centimeter air gap between the charging coils for reference purposes, after which the coil voltage coupling was measured using sheet material inserted between the inductive charging coils.

As illustrated in FIG. 17, there is an approximately +27 decibel voltage coupling increase in air when the frequency is increased from 8 kHz to 175 kHz. In contrast, when a 0.012 inch thick sheet of CP Ti Grade 1 is inserted between the induction coils, the increase in voltage coupling is only +7 decibels. As shown in FIG. 12, higher resistivity alloys (e.g., Ti-6Al-4V, ATI425) demonstrated higher coupling efficiencies at higher frequencies. Devices having housings formed from the ATI425 alloy provided better coil coupling as compared to those having housings formed from Ti-6Al-4V at all frequencies. Such improved coil coupling may be expected to provide improved telemetry distance as compared to devices having housings formed from CP Ti Grade 1 alloys. For example, it has been determined that the telemetry distance that may be achieved using an SP-700 alloy housing exceeds that which may be achieved using a CP Ti Grade 1 alloy by approximately 30 cm.

It is expected that various advantages may be obtained by utilizing the alloys described herein (e.g., Ti-6Al-4V, SP-700, ATI425, Ti811, Ti-3Al-2.5V, Ti6242, and titanium matrix composites (alpha and near alpha titanium matrix with SiC, TiC, TiO particles distributed therein)) to form at least a portion of housings for implantable medical devices. For example, devices using such alloys may have improved recharging efficiency (e.g., such devices may have an approximately 8 dB power coupling increase for recharging frequencies over 50 kHz as compared to devices having housings formed from CP Ti Grade 1 alloy). This may result in an approximately tenfold increase in power transfer.

Because the alloys used to form the housings have improved tensile strength as compared to Ti Grade 1, the portions of the housings using such materials may be formed having thinner walls, which contribute to the improved telemetry distance and power coupling efficiency. According to an exemplary embodiment, the housing includes portions having thicknesses of between approximately 0.01 and 0.016 inches. According to other exemplary embodiments, the portions have thicknesses of between approximately 0.01 and 0.012 inches.

While the various exemplary embodiments have been described in relation to IMDs in the form of implantable neurological stimulation devices, it should be noted that titanium alloys such as those described herein may be used in connection with other implantable medical devices as well, such as drug pumps, cardiac catheters, and the like. For example, the titanium alloys described herein may be used as a diaphragm material for an IMD in the form of an implantable pressure sensor (e.g., which may be integrated into a drug pump as a catheter diagnostic aid). Because diaphragms made from CP titanium (Ti) Grade 1 must be relatively thick, the signal to noise ratio of the sensor is relatively high. While the use of Ti-6Al-4V will help increase both strength and the signal to noise ratio, such an alloy is not available in sheets thin enough for practical sensors. The titanium alloys described herein offer the possibility of a sensor with higher signal to noise ratios that also meet the overpressure requirements for such components. The titanium alloys described herein may also find utility as housing materials for IMDs in the form of cardiac pacemakers.

As another example of a possible application, the titanium alloys described herein may be used as an outer shield for a drug pump. One advantageous feature of utilizing the alloys described herein is that it is believed that the use of such alloys may improve the efficiency of telemetry of the pump in a similar manner to that described above in the context of implantable INS devices.

While the preceding description has focused on housings for IMDs that are formed from different titanium materials, it should be noted that according to other exemplary embodiments, housings may be made from other biologically-compatible materials. For example, a housing may include a first portion formed from titanium and a titanium alloy and a second portion formed from a ceramic matrix material having a metal incorporated therein as reinforcement. In such a case, the edges of the ceramic matrix portion may be provided with metallic features (e.g., edges) configured to allow the portion to be welded to the titanium or titanium alloy portion (e.g., metal could be fused along the edges of the ceramic matrix portion).

It is important to note that the construction and arrangement of the implantable medical device as shown in the various exemplary embodiments is illustrative only. Although only a few embodiments of the present inventions have been described in detail in this disclosure, those skilled in the art who review this disclosure will readily appreciate that many modifications are possible without materially departing from the novel teachings and advantages of the subject matter recited in the claims. Accordingly, all such modifications are intended to be included within the scope of the present invention as defined in the appended claims. The order or sequence of any process or method steps may be varied or re-sequenced according to alternative embodiments. Other substitutions, modifications, changes and omissions may be made in the design, operating conditions and arrangement of the various exemplary embodiments without departing from the scope of the present invention as expressed in the appended claims.

What is claimed is:

1. A housing for an implantable medical device comprising:
    a first portion formed from a first material and aligned with a coil provided within the housing; and
    a second portion formed from a second material that differs from the first material;
    wherein the first material and the second material each comprise titanium and the first material has a higher resistivity than the second material; and
    wherein the second portion includes an aperture extending entirely through a generally planar region of a wall thereof at a first location, and the first portion is coupled to the second portion at the first location to seal the aperture, such that the first portion forms a part of the wall.

2. The housing of claim 1, wherein the first portion has a generally planar configuration.

3. The housing of claim 1, wherein the first portion is welded to the second portion.

4. The housing of claim 1, wherein the second material comprises commercial pure Grade 1 titanium.

5. The housing of claim 4, wherein the first material comprises an alloy having the formula Ti-4.5Al-3V-2Fe-2Mo-0.15O.

6. The housing of claim 4, wherein the first material comprises an alloy having the formula Ti-4Al-2.5V-1.5Fe-0.25O.

7. The housing of claim 4, wherein the first material comprises an alloy having the formula Ti-6Al-2Sn-4Zr-2Mo.

8. The housing of claim 4, wherein the first material comprises an alloy having the formula Ti-3Al-2.5V.

9. The housing of claim 4, wherein the first material comprises an alloy having the formula Ti-6Al-4V.

10. The housing of claim 4, wherein the first material comprises an alloy having the formula Ti-8Al-1Mo-1V.

11. The housing of claim 4, wherein the first material comprises a titanium matrix composite.

12. The housing of claim 1, wherein the first material is an alloy selected from the group consisting of Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

13. The housing of claim 12, wherein the second material is an alloy selected from the group consisting of Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

14. The housing of claim 1, wherein the second material is an alloy selected from the group consisting of Ti-4.5Al-3V-

2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

15. The housing of claim 1, wherein the second portion has a wall thickness of between approximately 0.001 and 0.016 inches.

16. The housing of claim 1, wherein at least a portion of the housing has a radius of curvature of between approximately 0.1 and 2.5 millimeters.

17. The housing of claim 1, wherein the second material exhibits greater formability as compared to a Ti-6Al-4V alloy.

18. The housing of claim 1, wherein the second material has better formability than the first material.

19. The housing of claim 1, wherein the housing is configured for use as the housing for an implantable neurological stimulation device.

20. The housing of claim 1, wherein the housing exhibits improved telemetry performance as compared to a housing made entirely of commercial pure titanium Grade 1.

21. The housing of claim 1, wherein the first portion has a higher resistivity than the second portion.

22. The housing of claim 1, wherein the wherein the second portion is not formed from the first material.

23. The housing of claim 22, wherein the first portion is not formed from the second material.

24. An implantable neurological stimulation device comprising:
a housing comprising a first portion and a second portion, the first portion and the second portion defining different regions of an innermost surface of the housing; and
a coil provided within the housing;
wherein the first portion comprises a first titanium material and the second portion comprises a second titanium material different from the first titanium material, the first portion being provided proximate the coil and having a higher resistivity than the second portion.

25. The implantable neurological stimulation device of claim 24, wherein the first portion has a generally planar configuration.

26. The implantable neurological stimulation device of claim 24, wherein the first portion is welded to the second portion.

27. The implantable neurological stimulation device of claim 24, wherein the first titanium material is an alloy selected from the group consisting of Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

28. The implantable neurological stimulation device of claim 27, wherein the second titanium material is an alloy selected from the group consisting of Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

29. The implantable neurological stimulation device of claim 27, wherein the second titanium material is commercial pure titanium Grade 1.

30. The implantable neurological stimulation device of claim 27, wherein the second titanium material is an alloy selected from the group consisting of Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

31. The implantable neurological stimulation device of claim 24, wherein the second portion has a wall thickness of between approximately 0.001 and 0.016 inches.

32. The implantable neurological stimulation device of claim 24, wherein at least a portion of the housing has a radius of curvature of between approximately 0.1 and 2.5 millimeters.

33. The implantable neurological stimulation device of claim 24, wherein the second titanium material has better formability than the first titanium material.

34. The implantable neurological stimulation device of claim 24, wherein the coil is a recharging coil.

35. The implantable neurological stimulation device of claim 24, wherein the coil is a telemetry coil.

36. A method of producing an implantable medical device comprising:
coupling a first member to a second member to form a housing, the first member comprising a first titanium material and the second member comprising a second titanium material that is different from the first titanium material, the first titanium material having a higher resistivity than the second titanium material;
removing a portion of the second member to form an aperture therein; and
providing a coil within the housing;
wherein the first member is provided proximate the coil, the aperture extends completely through a wall of the second member, and the first member is coupled to the second member at the aperture, such that the first member forms a part of the wall.

37. The method of claim 36, wherein the first member is coupled to the second member to seal the aperture.

38. The method of claim 36, wherein the step of coupling the first member to the second member comprises welding the first member to the second member.

39. The method of claim 36, wherein the first titanium material comprises Grade 1 titanium and the second titanium material is selected from the group consisting of Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

40. The method of claim 36, wherein the first titanium material and the second titanium material are each selected from the group consisting of Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

41. The method of claim 36, wherein the second titanium material is selected from the group consisting of Ti-4.5Al-3V-2Fe-2Mo-0.15O, Ti-4Al-2.5V-1.5Fe-0.25O, Ti-6Al-2Sn-4Zr-2Mo, Ti-3Al-2.5V, Ti-6Al-4V, Ti-8Al-1Mo-1V and combinations thereof.

42. The method of claim 36, wherein the second titanium material has better formability than the first titanium material.

43. The method of claim 36, wherein the second titanium material has greater percent elongation at room temperature as compared to the first titanium material.

44. The method of claim 36, wherein the coil is a telemetry coil.

45. The method of claim 36, wherein the coil is a recharging coil.

* * * * *

UNITED STATES PATENT AND TRADEMARK OFFICE
CERTIFICATE OF CORRECTION

| | | |
|---|---|---|
| PATENT NO. | : 8,380,311 B2 | Page 1 of 1 |
| APPLICATION NO. | : 11/590250 | |
| DATED | : February 19, 2013 | |
| INVENTOR(S) | : Li et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1185 days.

Signed and Sealed this
Twenty-sixth Day of August, 2014

Michelle K. Lee
*Deputy Director of the United States Patent and Trademark Office*